(12) United States Patent
True et al.

(10) Patent No.: US 9,114,250 B2
(45) Date of Patent: Aug. 25, 2015

(54) PINCH TO OPEN CUFF ELECTRODE

(71) Applicant: Cardiac Pacemakers, Inc., St. Paul, MN (US)

(72) Inventors: Kyle True, Minneapolis, MN (US); Brian Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 43 days.

(21) Appl. No.: 14/041,402

(22) Filed: Sep. 30, 2013

(65) Prior Publication Data

US 2014/0094888 A1  Apr. 3, 2014

Related U.S. Application Data

(60) Provisional application No. 61/709,152, filed on Oct. 2, 2012.

(51) Int. Cl.
*A61N 1/05* (2006.01)

(52) U.S. Cl.
CPC .................................. *A61N 1/0556* (2013.01)

(58) Field of Classification Search
None
See application file for complete search history.

(56) References Cited

U.S. PATENT DOCUMENTS

| 4,177,818 | A | 12/1979 | De Pedro |
| 4,573,481 | A | 3/1986 | Bullara |
| 4,590,946 | A | 5/1986 | Loeb |
| 4,590,949 | A | 5/1986 | Pohndorf |
| 4,602,624 | A | 7/1986 | Naples et al. |
| 4,628,942 | A | 12/1986 | Sweeney et al. |
| 4,740,170 | A | 4/1988 | Lee et al. |
| 4,920,979 | A | 5/1990 | Bullara |
| 4,940,065 | A | 7/1990 | Tanagho et al. |
| 4,979,511 | A | 12/1990 | Terry, Jr. |
| 5,031,621 | A | 7/1991 | Grandjean et al. |
| 5,095,905 | A | 3/1992 | Klepinski |

(Continued)

FOREIGN PATENT DOCUMENTS

| EP | 0585553 A1 | 6/1993 |
| JP | 2005058456 A | 3/2005 |

(Continued)

OTHER PUBLICATIONS

International Search Report and Written Opinion issued in PCT/US2014/015590, mailed May 28, 2014, 14 pages.

(Continued)

*Primary Examiner* — Erica Lee
(74) *Attorney, Agent, or Firm* — Faegre Baker Daniels LLP

(57) ABSTRACT

The invention describes a cuff electrode assembly and method for implanting that includes a resilient cuff body configured to be disposed about a nerve. The cuff body includes a first end portion and a second end portion. The cuff body can be pre-formed to define a closed configuration having a generally annular cross-sectional shape such that, in the closed configuration, the cuff body extends helically with the first and second end portions overlapping on different planes. The cuff electrode assembly includes a first arm member and a second arm member, each projecting radially outward from the cuff body and spaced from one another along the cuff body. The cuff body can be configured such that force applied to urge the first and second arm members toward one another causes relative deflection of the first end portion and the second end portion to define an open configuration of the cuff body.

20 Claims, 7 Drawing Sheets

(56) References Cited

U.S. PATENT DOCUMENTS

| | | |
|---|---|---|
| 5,215,089 A | 6/1993 | Baker et al. |
| 5,218,089 A | 6/1993 | Mariotti et al. |
| 5,251,634 A | 10/1993 | Weinberg |
| 5,259,394 A | 11/1993 | Bens |
| 5,282,468 A | 2/1994 | Klepinski |
| 5,324,322 A | 6/1994 | Grill, Jr. et al. |
| 5,334,438 A | 8/1994 | Saugnac |
| 5,344,438 A | 9/1994 | Testerman et al. |
| 5,351,394 A | 10/1994 | Weinberg |
| 5,358,516 A | 10/1994 | Myers et al. |
| 5,375,594 A | 12/1994 | Cueva |
| 5,505,201 A | 4/1996 | Grill et al. |
| 5,531,778 A | 7/1996 | Maschino et al. |
| 5,674,272 A | 10/1997 | Bush et al. |
| 5,689,877 A | 11/1997 | Grill et al. |
| 5,755,766 A | 5/1998 | Chastain et al. |
| 5,782,892 A | 7/1998 | Castle et al. |
| 5,871,530 A | 2/1999 | Williams et al. |
| 5,913,876 A | 6/1999 | Taylor et al. |
| 5,964,702 A | 10/1999 | Grill et al. |
| 6,038,479 A | 3/2000 | Werner et al. |
| 6,051,017 A | 4/2000 | Loeb et al. |
| 6,093,197 A | 7/2000 | Bakula et al. |
| 6,174,329 B1 | 1/2001 | Callol et al. |
| 6,178,349 B1 | 1/2001 | Kieval |
| 6,249,708 B1 | 6/2001 | Nelson et al. |
| 6,292,703 B1 | 9/2001 | Meier et al. |
| 6,296,659 B1 | 10/2001 | Foerster |
| 6,308,104 B1 | 10/2001 | Taylor et al. |
| 6,308,105 B1 | 10/2001 | Duysens et al. |
| 6,381,499 B1 | 4/2002 | Taylor et al. |
| 6,423,080 B1 | 7/2002 | Gellman et al. |
| 6,600,956 B2 | 7/2003 | Maschino et al. |
| 6,725,096 B2 | 4/2004 | Chinn et al. |
| 7,047,081 B2 | 5/2006 | Kuzma |
| 7,054,692 B1 | 5/2006 | Whitehurst et al. |
| 7,160,298 B2 | 1/2007 | Lawes et al. |
| 7,212,867 B2 | 5/2007 | Van Venroo |
| 7,502,650 B2 | 3/2009 | Kieval |
| 7,536,227 B1 | 5/2009 | Poore et al. |
| 7,561,923 B2 | 7/2009 | Libbus et al. |
| 7,711,421 B2 | 5/2010 | Shafer et al. |
| 7,749,273 B2 | 7/2010 | Cauthen, III et al. |
| 7,807,925 B2 | 10/2010 | Zarembo |
| 7,831,311 B2 | 11/2010 | Cross, Jr. et al. |
| 7,891,085 B1 | 2/2011 | Kuzma et al. |
| 7,925,352 B2 | 4/2011 | Stack et al. |
| 7,925,358 B2 | 4/2011 | Belden et al. |
| 7,933,662 B2 | 4/2011 | Marshall et al. |
| 7,957,817 B1 | 6/2011 | Gillespie et al. |
| 7,974,706 B2 | 7/2011 | Moffitt et al. |
| 7,996,092 B2 | 8/2011 | Mrva et al. |
| 8,100,141 B2 | 1/2012 | Slupecki et al. |
| 8,155,757 B1 | 4/2012 | Neisz et al. |
| 8,244,372 B1 | 8/2012 | Zhulati et al. |
| 8,295,948 B2 | 10/2012 | Barker et al. |
| 8,326,418 B2 | 12/2012 | Sommer et al. |
| 8,417,343 B2 | 4/2013 | Bolea et al. |
| 8,452,406 B2 | 5/2013 | Arcot-Krishnamurthy et al. |
| 8,483,845 B2 | 7/2013 | Sage |
| 8,548,593 B2 | 10/2013 | Ternes et al. |
| 8,639,355 B2 | 1/2014 | Soltis |
| 2002/0116042 A1 | 8/2002 | Boling |
| 2002/0128700 A1 | 9/2002 | Cross, Jr. |
| 2003/0040785 A1 | 2/2003 | Maschino et al. |
| 2003/0236558 A1 | 12/2003 | Whitehurst et al. |
| 2004/0010303 A1 | 1/2004 | Bolea et al. |
| 2004/0111139 A1 | 6/2004 | McCreery |
| 2005/0209655 A1 | 9/2005 | Bradley et al. |
| 2005/0234512 A1 | 10/2005 | Nakao |
| 2005/0283246 A1 | 12/2005 | Cauthen, III et al. |
| 2006/0030919 A1 | 2/2006 | Mrva et al. |
| 2006/0122675 A1 | 6/2006 | Libbus et al. |
| 2006/0190042 A1 | 8/2006 | Stone et al. |
| 2006/0259078 A1 | 11/2006 | Libbus |
| 2007/0071568 A1 | 3/2007 | Dorstewitz |
| 2007/0083236 A1 | 4/2007 | Sikora et al. |
| 2007/0100406 A1 | 5/2007 | Kollatschny et al. |
| 2007/0118177 A1 | 5/2007 | Libbus et al. |
| 2007/0142871 A1 | 6/2007 | Libbus et al. |
| 2007/0173914 A1 | 7/2007 | Kollatschny |
| 2007/0203556 A1 | 8/2007 | Rutten et al. |
| 2007/0239243 A1 | 10/2007 | Moffitt et al. |
| 2007/0255320 A1 | 11/2007 | Inman et al. |
| 2008/0046058 A1 | 2/2008 | Cross et al. |
| 2008/0051839 A1 | 2/2008 | Libbus et al. |
| 2008/0058871 A1 | 3/2008 | Libbus et al. |
| 2008/0058874 A1 | 3/2008 | Westlund et al. |
| 2008/0058901 A1 | 3/2008 | Ternes et al. |
| 2008/0086181 A1 | 4/2008 | Amurthur et al. |
| 2008/0091255 A1 | 4/2008 | Caparso et al. |
| 2008/0103407 A1 | 5/2008 | Bolea et al. |
| 2008/0103545 A1 | 5/2008 | Bolea et al. |
| 2008/0132987 A1 | 6/2008 | Westlund et al. |
| 2008/0140092 A1 | 6/2008 | Stone et al. |
| 2008/0172101 A1 | 7/2008 | Bolea et al. |
| 2008/0177365 A1 | 7/2008 | Bolea et al. |
| 2008/0177366 A1 | 7/2008 | Bolea et al. |
| 2008/0183258 A1 | 7/2008 | Inman |
| 2008/0195188 A1 | 8/2008 | Libbus et al. |
| 2008/0234780 A1 | 9/2008 | Smith et al. |
| 2008/0255613 A1 | 10/2008 | Kaiser et al. |
| 2009/0048641 A1 | 2/2009 | Libbus |
| 2009/0210042 A1 | 8/2009 | Kowalczewski |
| 2009/0259260 A1 | 10/2009 | Bentley et al. |
| 2009/0275997 A1 | 11/2009 | Faltys et al. |
| 2009/0276024 A1 | 11/2009 | Bonde et al. |
| 2009/0318961 A1 | 12/2009 | Stone et al. |
| 2010/0023088 A1 | 1/2010 | Stack et al. |
| 2010/0036451 A1 | 2/2010 | Hoffer |
| 2010/0121405 A1 | 5/2010 | Ternes et al. |
| 2010/0145221 A1* | 6/2010 | Brunnett et al. ............... 600/554 |
| 2010/0168831 A1 | 7/2010 | Korivi et al. |
| 2010/0211131 A1 | 8/2010 | Williams et al. |
| 2010/0286553 A1 | 11/2010 | Feler et al. |
| 2010/0305674 A1 | 12/2010 | Zarembo et al. |
| 2010/0312320 A1 | 12/2010 | Faltys et al. |
| 2010/0331938 A1 | 12/2010 | Sommer et al. |
| 2011/0004281 A1 | 1/2011 | Jones |
| 2011/0022142 A1 | 1/2011 | Barker et al. |
| 2011/0040257 A1 | 2/2011 | Behymer et al. |
| 2011/0060395 A1 | 3/2011 | Cantlon |
| 2011/0172682 A1 | 7/2011 | Brady et al. |
| 2011/0172701 A1 | 7/2011 | Wales et al. |
| 2012/0022617 A1 | 1/2012 | Tockman et al. |
| 2012/0035691 A1 | 2/2012 | Tockman et al. |
| 2012/0065702 A1 | 3/2012 | Arcot-Krishnamurthy et al. |
| 2012/0221087 A1 | 8/2012 | Parnis et al. |
| 2013/0005169 A1 | 1/2013 | Soltis et al. |
| 2013/0013045 A1 | 1/2013 | Soltis |
| 2013/0172973 A1 | 7/2013 | Tockman et al. |
| 2013/0253615 A1 | 9/2013 | Arcot-Krishnamurthy, Shantha et al. |
| 2013/0253624 A1 | 9/2013 | Tockman et al. |

FOREIGN PATENT DOCUMENTS

| | | |
|---|---|---|
| JP | 2008526299 A | 7/2008 |
| WO | WO9929366 A1 | 6/1999 |
| WO | WO2004052176 A2 | 6/2004 |
| WO | WO2006093685 A1 | 9/2006 |
| WO | WO2007024164 A1 | 1/2007 |
| WO | WO2008088798 A1 | 7/2008 |
| WO | WO2008094349 A1 | 8/2008 |
| WO | WO2009020639 A1 | 2/2009 |
| WO | WO2009025817 A2 | 2/2009 |
| WO | WO2009100242 A2 | 8/2009 |
| WO | WO2011053766 A1 | 5/2011 |
| WO | 2013142053 A1 | 9/2013 |

OTHER PUBLICATIONS

International Search Report and Written Opinion issued in PCT/US2013/077949, mailed Jun. 20, 2014, 15 pages.

(56) References Cited

OTHER PUBLICATIONS

Kirsch, Robert F. et al., "Restoration of Hand and Arm Function by Functional Neuromuscular Stimulation", Period covered: Jun. 1, 2001-Aug. 31, 2006, 71 pages.
International Search Report and Written Opinion Issued in PCT/US2009/063442, mailed Feb. 1, 2010, 11 pages.
International Search Report and Written Opinion Issued in PCT/US2010/026350, mailed Jun. 2, 2010.
International Search Report and Written Opinion Issued in PCT/US2011/020699, mailed Jul. 26, 2011, 24 pages.
International Search Report and Written Opinion Issued in PCT/US2011/049585, mailed Dec. 19, 2011.
International Search Report and Written Opinion Issued in PCT/US2012/044020, mailed Sep. 11, 2012, 9 pages.
International Search Report and Written Opinion issued in PCT/US2012/044028, mailed Oct. 1, 2012, 9 pages.
International Search Report and Written Opinion issued in PCT/US2012/071812, mailed Sep. 13, 2013, 12 pages.
International Search Report and Written Opinion issued in PCT/US2013/029306, mailed Jul. 18, 2013, 13 pages.
International Search Report and Written Opinion issued in PCT/US2013/062560, mailed Dec. 17, 2014, 13 pages.
International Search Report and Written Opinion issued in PCT/US2013/062608, mailed Dec. 17, 2014, 13 pages.
Partial International Search Report issued in PCT/US2011/020699, mailed Mar. 24, 2011, 6 pages.
International Preliminary Examination Report, Chapter II, issued in PCT/US2013/029306, completed Aug. 19, 2014, 16 pages.
Written Opinion of the International Preliminary Examining Authority issued in PCT/US2013/029306, mailed May 8, 2014, 6 pages.

* cited by examiner

PINCH TO OPEN CUFF ELECTRODE

CROSS-REFERENCE TO RELATED APPLICATION

This application claims priority to U.S. Provisional Application 61/709,152, filed Oct. 2, 2012, which is herein incorporated by reference in its entirety.

TECHNICAL FIELD

The present disclosure relates to implantable medical devices and method of implantation of such devices. More specifically, the disclosure relates to cuff electrode assemblies for implantation around a nerve.

BACKGROUND

Various types of electrodes can be used for providing electrical stimuli to a target location inside the body. One of them is a cuff shaped electrode, shaped as per the geometry of a typical nerve or nerve fiber having a generally annular shape. Cuff shaped electrodes are designed to provide stimulation or record an electro-gram from tissues/peripheral nerves. The cuff shaped electrodes can generally include a dielectric material and defines a lumen having a sufficient diameter to receive a nerve that needs to be electrically stimulated. There exists a continuing need for improved cuff electrode assemblies.

SUMMARY

In Example 1, a cuff electrode assembly for implantation on a target nerve, the cuff electrode assembly comprising a resilient cuff body, first and second arm members, and an electrode. The cuff body is configured to be disposed about the target nerve, and includes a first end portion having a first free end, and a second end portion having a second free end, wherein the cuff body is pre-formed to define a closed configuration having a generally annular cross-sectional shape. In the closed configuration the cuff body extends helically with the first and second end portions overlapping one another in different planes. The first arm member and the second arm member each project radially outward from the cuff body and are spaced from one another along the cuff body, wherein the cuff body is configured such that a force applied to urge the first and second arm members toward one another causes relative deflection of the second free end and the first free end so as to define an open configuration of the cuff body configured to allow the cuff body to be positioned around the target nerve. The electrode is disposed at least partially within or on the cuff body oriented to provide an electrical stimuli to the target nerve when the cuff body is disposed about the target nerve.

In Example 2, the cuff electrode assembly of Example 1, wherein the cuff body is configured to extend greater than 360 degrees about the target nerve when placed thereon in the closed configuration.

In Example 3, the cuff electrode assembly of either of Examples 1 or 2, wherein the first arm member and the second arm member and a portion of the cuff body proximate the first arm member and the second arm member define a pinch hinge portion of the cuff electrode assembly, wherein a force applied to urge the first and second arm members toward one another is operable to reduce a degree of circumferential overlap of the first end portion and the second end portion.

In Example 4, the cuff electrode assembly of Example 3, wherein the first arm member and the second arm member form a hinge angle with the pinch hinge portion, and wherein the hinge angle is less than 180 degrees while the cuff body is in the closed configuration.

In Example 5, the cuff electrode assembly of either of Examples 3 or 4, wherein the pinch hinge portion is located substantially equidistant from the first free end and the second free end.

In Example 6, the cuff electrode assembly of either of Examples 3 or 4, wherein the pinch hinge portion is located closer to the first free end than to the second free end.

In Example 7, the cuff electrode assembly of any of Examples 1-6, wherein the cuff body is made substantially of a flexible, electrically insulating polymer.

In Example 8, the cuff electrode assembly of Example 7, wherein the flexible insulating polymer is silicone rubber.

In Example 9, the cuff electrode assembly of either of Examples 7 or 8, wherein the cuff body further includes a reinforcing material in the flexible, electrically insulating polymer.

In Example 10, the cuff electrode assembly of any of Examples 7-9, wherein the cuff body further includes a stiffening member within the flexible, insulating polymer.

In Example 11, the cuff electrode assembly of any of Examples 1-10, further comprising a stiffening member configured to urge the cuff body to return to the pre-formed closed configuration upon release of a force causing the cuff body to assume the open configuration.

In Example 12, an implantable lead assembly for stimulating a target nerve, the lead assembly comprising at least one cuff electrode assembly, a flexible lead body, an insulated flexible conductor member, and a connector assembly. The at least one cuff electrode assembly comprises a resilient cuff body, first and second arm members, and an electrode. The cuff body is configured to be disposed about the target nerve, and includes a first end portion having a first free end, and a second end portion having a second free end, wherein the cuff body is pre-formed to define a closed configuration having a generally annular cross-sectional shape. In the closed configuration the cuff body extends helically with the first and second end portions overlapping one another in different planes. The first and second arm members each project radially outward from the cuff body and are spaced from one another along the cuff body, wherein the cuff body is configured such that a force applied to urge the first and second arm members toward one another causes relative deflection of the second free end and the first free end so as to define an open configuration of the cuff body configured to allow the cuff body to be positioned around the target nerve. The electrode is disposed at least partially within or on the cuff body and is oriented to provide an electrical stimuli to the target nerve when the cuff body is disposed about the target nerve. The lead body is made of an insulative material, and has a proximal end portion and a distal end portion. The conductor member is at least partially disposed within the lead body, and includes a distal end electrically and mechanically coupled to the electrode of the cuff electrode assembly. The connector assembly is coupled to the proximal end portion of the lead body and to the conductor member, the connector assembly configured to electrically couple the conductor member to an implantable stimulator.

In Example 13, the lead assembly of Example 12, wherein the at least one cuff electrode assembly includes a plurality of cuff electrode assemblies, and wherein the lead further includes a plurality of insulated, flexible conductor members at least partially disposed within the lead body, and wherein an electrode of each of the plurality of cuff electrode assemblies is electrically and mechanically coupled to one of the plurality of conductor members.

In Example 14, the lead assembly of Example 13, wherein the plurality of cuff electrode assemblies are configured to be opened and implanted simultaneously.

In Example 15, the cuff electrode assembly of any of Examples 12-14, wherein the cuff body is made substantially of a flexible, electrically insulating polymer.

In Example 16, the cuff electrode assembly of Example 15, wherein the cuff body further includes a stiffening member within the flexible, insulating polymer.

In Example 17, a method for implanting a cuff electrode assembly on a target nerve. The cuff electrode assembly includes a resilient cuff body, first and second arm members and an electrode. The cuff body is configured to be disposed about the target nerve, and includes a first end portion having a first free end, and a second end portion having a second free end, wherein the cuff body is pre-formed to define a closed configuration having a generally annular cross-sectional shape, wherein in the closed configuration the cuff body extends helically with the first and second end portions overlapping one another in different planes. The first and second arm members each project radially outward from the cuff body and are spaced from one another along the cuff body, wherein the cuff body is configured such that a force applied to urge the first and second arm members toward one another causes relative deflection of the second free end and the first free end so as to define an open configuration of the cuff body configured to allow the cuff body to be positioned around the target nerve. The electrode is disposed at least partially within or on the cuff body oriented to provide an electrical stimuli to the target nerve when the cuff body is disposed about the target nerve. The method comprises inserting the cuff electrode assembly within a patient's body, and applying a force to at least one of the first and second arm members to urge together the first and second arm members thereby causing the first and second free ends to deflect such that the cuff body assumes the open configuration. The method next comprises placing the cuff electrode assembly proximate the target nerve such that the cuff body at least partially surrounds the target nerve, and then releasing the force to cause or allow the cuff body to close and thereby wrap substantially 360 degrees around the target nerve.

In Example 18, the method of Example 17, wherein the cuff electrode assembly further includes a stiffening member within the cuff body configured to stiffen the cuff body while being opened upon application of the force, and further configured to allow the cuff body to return to its closed configuration, upon removal of the force. In addition, the stiffening member is also configured to maintain the cuff body in its closed configuration around the target nerve upon removal of the force such that the first end portion and the second end portion overlap with each other in different planes.

In Example 19, the method of either of Examples 17 or 18, wherein the cuff electrode assembly is a first cuff electrode assembly of an implantable lead assembly including one or more additional cuff electrode assemblies, the one or more additional cuff electrode assemblies being coupled to the first cuff electrode assembly.

In Example 20, the method of Example 19, wherein the method further comprises simultaneously opening the first cuff electrode assembly and the one or more additional cuff electrode assemblies.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
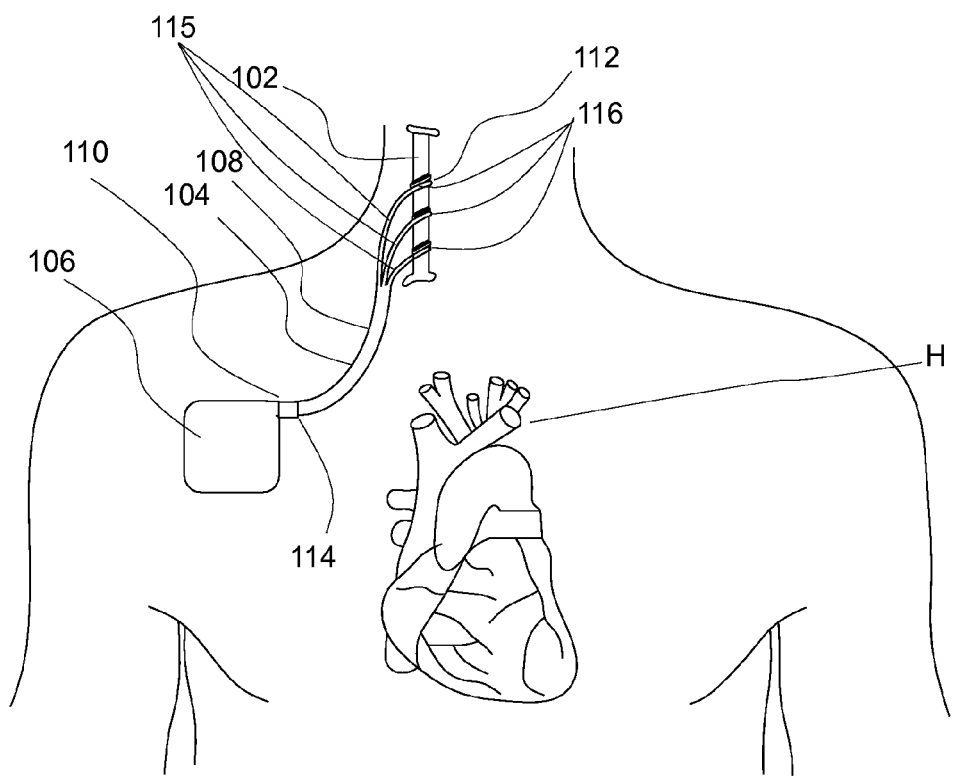
FIG. 1 is a schematic illustration of a system in an implanted state, according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system 100 for stimulating a target nerve 102 As shown, the system 100 includes an implantable lead assembly 104 coupled to an implantable medical device (IMD) 106. In the illustrated embodiment, the lead assembly 104 includes a lead body 108 having a proximal end portion 110 and a distal end portion 112, a connector assembly 114, a plurality of insulated conductor members 115, and a plurality of cuff electrode assemblies 116. In the various embodiments, each of the conductor members 115 can be partially disposed within the lead body 108 and extend distally from the distal end portion 112 thereof. As further shown, each of the cuff electrode assemblies 116 is coupled to one of the conductor members 115. In addition, in the illustrated embodiment, the connector assembly 114 is coupled to and extends from the proximal end portion 110 of the lead body 108. The connector assembly 114 is operable to mechanically couple the lead assembly 104 to the IMD 106, and also to electrically couple each of the conductor members 115 to electronics within the IMD 106. In various embodiments, the connector assembly 114 can be a multipolar connector, with a plurality of electrical contacts (not shown) each electrically connected to a respective one of the conductor member 115.

During operation, the lead assembly 104 delivers electrical signals between the IMD 106 and the cuff electrode assemblies 116, which are configured to wrap around and thereby be secured to the target nerve 102. In various embodiments, the cuff electrode assemblies 116 can be separately controlled by the IMD 106, such that energy having different magnitude, phase, and/or timing characteristics may be delivered to or from each of the cuff electrode assemblies 116. While the lead assembly 104 shown includes three cuff electrode assemblies 116, more or fewer electrode assemblies 116 can alternatively be employed in the system 100. In addition, one or more of the cuff electrode assemblies 116 may alternatively be configured as a strain relief cuff that does not carry electrical signals, but secures the lead assembly 104 relative to the nerve 102 to minimize movement of the active cuff electrode assemblies 116 relative to the excitable tissue due to voluntary or involuntary movements of the patient. Furthermore, the IMD 106 shown is merely by way of illustration. In various embodiments, the IMD 106 may have other configurations suitable for use in conjunction with the lead assembly and may be implanted in a suitable location in the patient's body. The IMD 106 can be implanted subcutaneously within the body, typically at a location such as in a patient's chest or abdomen, although other implantation locations are possible.

In various embodiments, the system 100 can be configured to sense and stimulate the sympathetic and/or parasympathetic nervous systems. Stimulating the sympathetic and parasympathetic nervous systems can have effects on physiological parameters associated with the heart H, such as heart rate and blood pressure. In addition, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intestine, increases urine secretion, and contracts the wall and relaxes the sphincter of the bladder. The functions associated with the sympathetic and parasympathetic nervous systems are many and can be complexly integrated with each other.

In one embodiment, the target nerve 102 is the vagus nerve, and specifically, the right vagus nerve. In such embodiments, the cuff electrode assemblies 116 can be arranged around the vagus nerve 102, with the IMD 106 configured to deliver energy to the cuff electrode assemblies 116 to stimulate the vagus nerve 102. The vagus nerve has afferent properties, such that the neural stimulation is transmitted to the central nervous system (CNS). Vagal stimulation simultaneously increases parasympathetic and decreases sympathetic activity, and is believed to prevent further remodeling or predisposition to fatal arrhythmias in post-myocardial infarction (MI) patients, to help restore autonomic balance and increase heart rate variability (HRV), increase parasympathetic and reduce sympathetic tone in hypertrophic cardiac myopathy (HCM), neurogenic hypertension, and arrhythmia protection, reduce anginal symptoms, to increase coronary blood flow (CBF), and prevent development or worsening of congestive heart failure (CHF) following MI. The cuff electrode assemblies 116 can be configured and arranged to stimulate the vagus nerve N to provide the physiological responses described. While the cuff electrode assemblies 116 are shown arranged around the right vagus nerve 102 in FIG. 1, the cuff electrode assemblies 116 can be configured and arranged to stimulate the left vagus nerve to treat other physiological and psychological conditions, such as epilepsy and depression.

Figure 2:
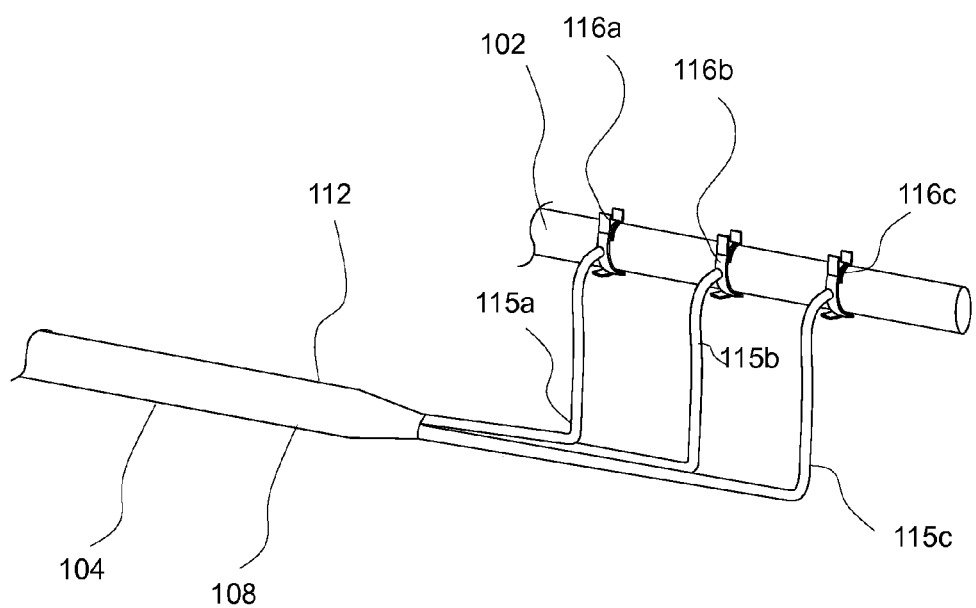
FIG. 2 is a schematic illustration of a lead assembly included in the system of FIG. 1, according to an embodiment of the present invention.

FIG. 2 is a schematic perspective view a portion of the implantable lead assembly 104 showing the cuff electrode assemblies 116 wrapped about the target nerve 102. In the particular embodiment shown in FIG. 2, the lead assembly 104 includes three cuff electrode assemblies 116a, 116b, 116c, and also three conductor members 115a, 115b, 115c each extending distally with respect to the lead body distal end portion 112 and coupled to a corresponding one of the cuff electrode assemblies. As discussed previously, however, in other embodiments, more or fewer of the cuff electrode assemblies 116 and the conductor members 115 can be utilized in a given lead assembly 104.

As will be explained in greater detail herein, the cuff electrode assemblies 116a, 116b, 116c are each configured to be manipulated during implantation so that they can be disposed over the nerve 102, and thereafter substantially wrap around the target nerve 102 while applying sufficient radial and frictional forces against the nerve 102 so as to retain themselves in the implantation position selected by the clinician. Additionally, each cuff electrode assembly 116a, 116b, 116c includes an electrode (not shown in FIG. 1 or 2) oriented toward the nerve 102 to provide the selected therapeutic stimuli thereto.

In various embodiments, the insulated conductor members 115a, 115b, 115c each includes an inner conductor element (not shown) covered by an outer insulating layer that operates to electrically isolate the inner conductor element from the outside environment. Each of the conductor elements is electrically coupled to the electrode of one of the cuff electrode assemblies 116a, 116b, 116c.

In various embodiments, the lead body 108 can be formed of an electrically insulative material and can also be operable to electrically isolate the various conductor members 115a, 115b, 115c from the external environment, as well as to provide structural support for the lead assembly 104 as a whole. In various embodiments, the insulating layers of the conductor members 115a, 115b, 115c can be integrally formed with the lead body 108. Alternatively, the lead body 108 can initially be a separate, tubular element and the insulated conductor members 115a, 115b, 115c can thereafter be strung through the lead body 108. The conductor elements of the conductor members 115a, 115b, 115c can be of a configuration providing the requisite electrical and mechanical properties for a particular lead assembly 104. In various embodiments, such conductor elements can be single or multi-filar conductor coils. In various embodiments, the conductor elements can be single or multi-strand cable conductors.

Exemplary materials for use in the lead body 104 and the conductor member electrical insulating layers include, without limitation, polymeric materials such as styrene isoprene butadiene (SIBS), polytetrafluoroethylene (PTFE), polyethylene (PE), polypropylene (PP), fluorinated ethylene propylene (FEP), ethylene-tetrafluoroethylene (ETFE), or another biocompatible polymer. Exemplary materials for the conductor elements can include, without limitation, MPTa, Pt-clad Ta, Pt-clad MP35N, MP35N, low-titanium MP35N, MPAg, and Nitinol. It is emphasized, however, that the foregoing insulator and conductor materials are included for illustration purposes only and are in no way intended to be exhaustive listings of the suitable materials that can be utilized.

Figure 3A:
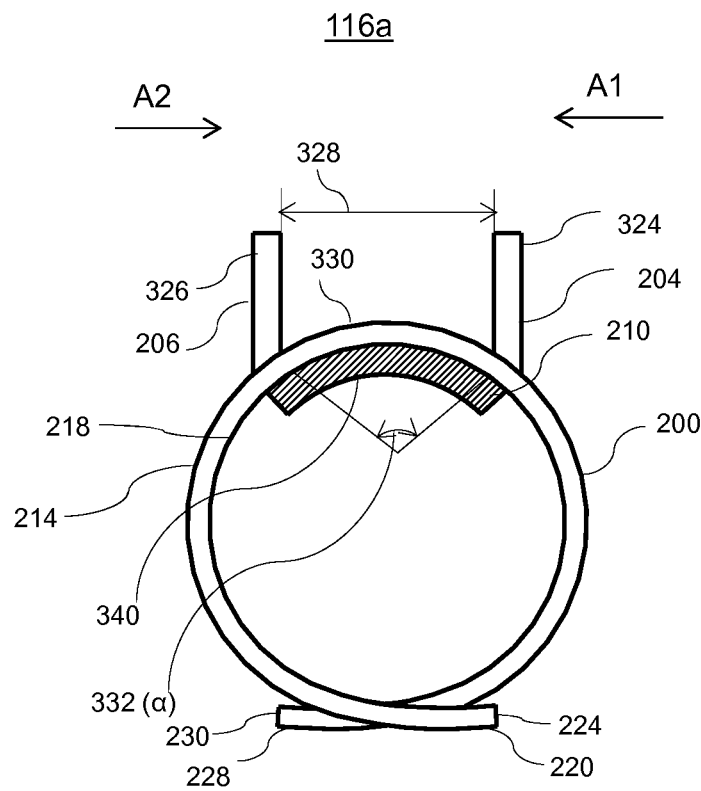
FIG. 3A shows a schematic front view of a cuff electrode assembly included in the system of FIG. 1 that can be used in relation to embodiments of the present invention.
Figure 3B:
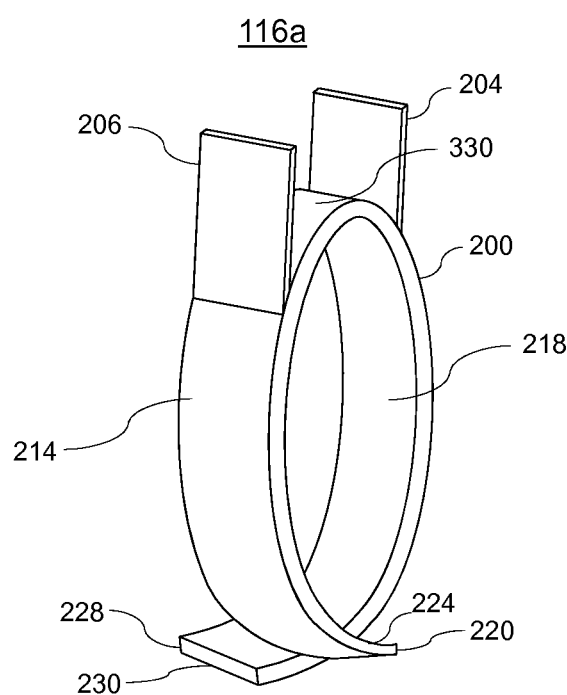
FIG. 3B shows a schematic perspective view of the cuff electrode assembly of FIG. 3A in relation to embodiments of the present invention.
Figure 4:
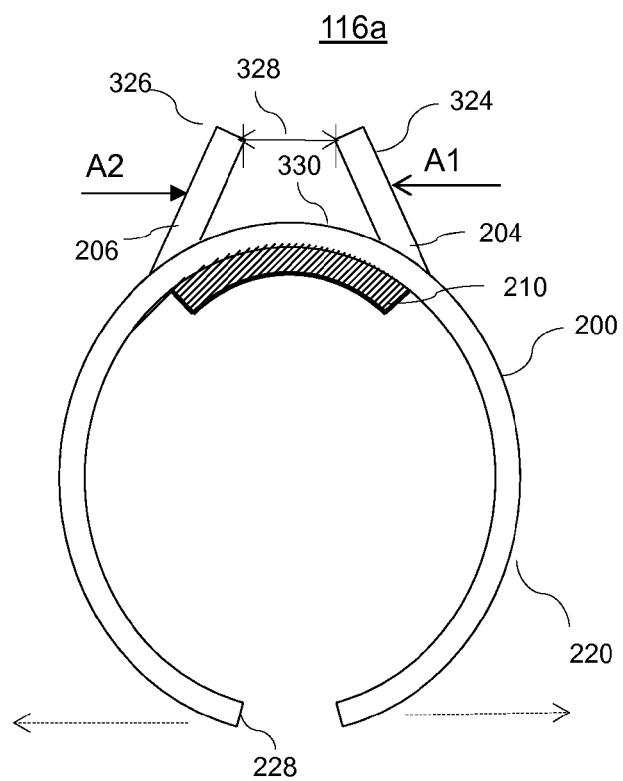
FIG. 4 shows a schematic front view of the cuff electrode assembly of FIG. 3A in an open configuration in relation to embodiments of the present invention.

FIGS. 3A and 3B are, respectively schematic end and perspective views of the cuff electrode assembly 116a in a closed configuration (i.e., the configuration assumed in its implanted state around a target nerve, similar to the target nerve 102), and FIG. 4 is a schematic end view of the cuff electrode assembly 116a in an open configuration (i.e., the configuration assumed so as to allow the clinician to place the cuff electrode assembly 116a around the target nerve 102). It will be appreciated that the cuff electrode assemblies 116b, 116c can be configured in substantially the same or an identical manner as the cuff electrode assembly 116a.

As shown, the cuff electrode assembly 116a includes a resilient cuff body 200, a pair of arm members 204, 206, and an electrode 210. In addition, the cuff body 200 includes an outer surface 214, an inner surface 218, a first end portion 220 having a first free end 224, and a second end portion 228 having a second free end 230. The cuff body 200 further has a length extending between the first and second free ends 224, and 230. As further shown, the arm members 204 and 206 extend from the cuff body 200 radially outward from the outer surface 218 thereof, and are spaced from one another along the cuff body 200. In addition, the electrode 210 is positioned on the inner surface 218 such that it can be oriented toward and/or against the target nerve 102 (see FIGS. 1-2) when the cuff electrode assembly 116 is placed thereupon.

As further shown, the cuff body 200 assumes in its closed configuration, when viewed in the end view of FIG. 3A, a generally annular cross-sectional shape. In addition, and as can be seen in FIG. 3A, the length of the cuff body 200 generally has a helical configuration, such that, in the closed configuration, the first and second free ends 224, and 230 overlap one another in different planes transverse to a longitudinal axis of the cuff electrode assembly 116a. In various embodiments, the cuff body 200 is pre-formed to tend to assume the closed configuration shown in FIGS. 3A and 3B in the absence of an external force urging all or a portion of the cuff body 200 to a different configuration. In various embodiments, the cuff body 200 can be configured to cover greater than 360 degrees about the target nerve when placed thereon in the closed configuration, as shown in FIGS. 3A and 3B.

The cuff body 200 can be configured such that a force applied to urge the first arm member 204 and the second arm member 206 toward one another causes relative deflection of the first free end 224 and the second free end 230 so as to define an open configuration of the cuff body 200 as shown in FIG. 4. The open configuration can allow the cuff body 200 to be positioned around the target nerve. Upon subsequent removal of the aforementioned force, the cuff body 200 can then attempt to resume its closed configuration, thus applying a radial force on the target nerve 102 to secure the cuff electrode assembly 116a in place.

In an embodiment, the first arm member 204 can include a distal portion 324 and the second arm member 206 can include a distal portion 326. In use, a force can be applied to the distal portion 324 of the first arm member 204 and the distal portion 326 of the second arm member 206 so as to achieve the open configuration. For example, the force can be applied on the first arm member 204 such as along a direction A1 and on the second arm member 206 such as along a direction A2. In an embodiment, the distal portion 324 of the first arm member 204 and the distal portion 326 of the second arm member 206 can be separated by an arm member distance 328 such as shown in FIG. 3A, while the assembly is in the completely closed state without any force applied thereon. The arm member distance 328 can be subject to a change in dimension depending upon the magnitude of the force applied on the arm members. The force can be applied to urge the first arm member 204 and the second arm member 206 toward one another so as to reduce the arm member distance 328. This in turn results in deflection of the first and second free ends 224, 230 from their positions when in the closed configuration, and also reduces a degree of circumferential overlap of the first end portion 220 and the second end portion 230.

In an embodiment, the first arm member 204 and the second arm member 206 and a portion of the cuff body 200 proximate to the first arm member 204 and the second arm member 206 define a pinch hinge portion 330 of the cuff electrode assembly 116. In an embodiment, the pinch hinge portion 330 can be defined by a portion separated by the arm member distance 328 and includes a portion length 340, wherein the portion length 340 can be configured along a portion of the cuff body 200. The pinch hinge portion 330 can be configured to allow the first arm member 204 and the second arm member 206 to form a hinge angle 332 (α) such that the hinge angle 332 (α) can be less than 180 degrees while the cuff body 200 assumes the completely closed configuration without any force applied thereon. In the illustrated embodiment, the pinch hinge portion 330 is located substantially equidistant from the first free end 224 and the second free end 230. In various other embodiments, the pinch hinge portion 330 can be located closer to one of the first and second free ends 224, 230 than to the other of the first and second free ends 224, 230.

In an embodiment, the electrode 210 is disposed at least partially within or on the cuff body 200. The electrode 210 can be oriented to provide electrical stimuli to the target nerve when the cuff body 200 is disposed at the target nerve. In an embodiment, the electrode 210 can be disposed at any portion of the length of the cuff body 200 to provide electrical stimuli and sensing to the target nerve such as the vagus nerve. In various embodiments, the cuff electrode assembly 116a can include one or a plurality of the electrodes 110. Exemplary materials used for the electrode 210 can include, without limitation, platinum, titanium, iridium, and alloys of any of the foregoing.

In an embodiment, the design of the cuff electrode assembly 116a is simple and easy to operate such that a clinician does not need any specific training to close or open or to modify the cuff electrode assembly 116a. In an example, the cuff electrode assembly 116a can be configured to be actuated directly by manipulating the cuff body 200 and the first and second arm members 204, 206. In an example, the cuff electrode assembly 116a can be configured to be actuated by an implant tool (not shown). In various embodiments, an implant tool can be configured to simultaneously apply a force to all arm members of all the cuff assemblies 116 on a given lead assembly 104 so that all such cuff electrode assemblies 116 can be deployed on the target nerve simultaneously.

As discussed previously, in various embodiments, the cuff body 200 is pre-formed to tend to assume the closed configuration shown in FIGS. 3A and 3B. Thus, once the external force causing the cuff body 200 to assume the open configuration is removed, the cuff body 200 will tend to transition back to its closed configuration. In various embodiments, the cuff body 200 can be formed of a polymeric material that provides sufficient resiliency to allow the cuff body 200 to be deflected toward the open configuration and thereafter return to the pre-formed, closed configuration. In one embodiment, the cuff body 200 can be made from a silicone rubber. In various embodiments, the cuff body 200 can include additional structure, e.g., additives or reinforcing elements incorporated or embedded into the polymeric material to enhance mechanical strength and/or resiliency of the cuff body 200. The cuff electrode assembly 116a is described herein merely for descriptive and exemplary purposes, however other cuff electrode assemblies such as 116b and 116c may also be designed, placed, and employed in a similar manner, without limitations.

Figure 5:
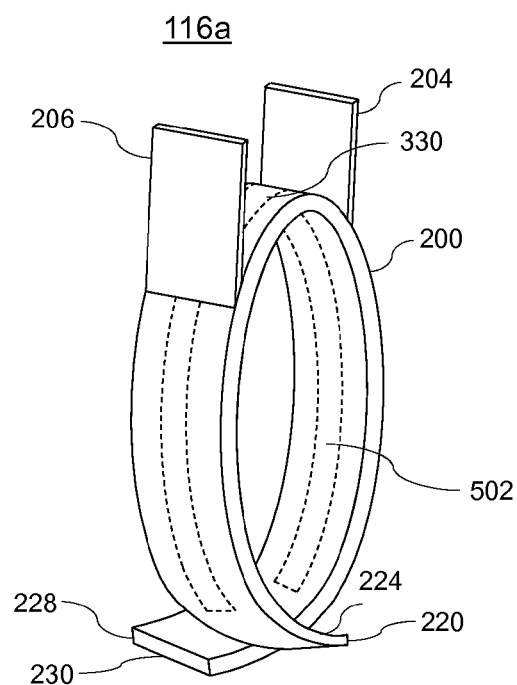
FIG. 5 shows a schematic perspective view of the cuff electrode assembly of FIG. 3A, showing a stiffening mechanism in relation to embodiments of the present invention.

FIG. 5 shows a schematic perspective view of an alternative embodiment of the cuff electrode assembly 116a, including a stiffening member 502 incorporated into the polymeric cuff body 200. In the illustrated embodiment, the stiffening member 502 is in the form of a ribbon of material embedded in the polymeric material forming the remainder of the cuff body 200. In various embodiments, the stiffening member 502 can be made of a polymeric or metallic material sized and shaped to provide a desired degree of stiffness and resiliency to the cuff body 200. In various embodiments, the stiffening member 502 is pre-formed so as to cause the cuff body 200 to close upon removal of the externally applied force urging the first and second end arm members 204 and 206 toward one another as discussed previously. In such embodiments, the stiffening member 502 can be configured to maintain the cuff body 200 in the closed configuration, substantially surrounding the target nerve upon removal of the opening force on the arm members 204, 206.

In various embodiments, the stiffening member 502 can be a metallic, electrically conductive element that also operates as the electrode for the cuff electrode assembly 116a. Exemplary materials for use as the stiffening member 502 include, without limitation, nickel-titanium alloys such as nitinol, stainless steels, platinum alloys, and the like. In such embodiments, an inner surface of the stiffening member 502 can be exposed so as to be capable of contact with the target nerve when the cuff electrode assembly is placed thereupon. Additionally, in such embodiments, the stiffening member 502 is electrically coupled to the conductor element of a conductor member such as the conductor member 115a (see FIGS. 1-2).

Figure 6A:
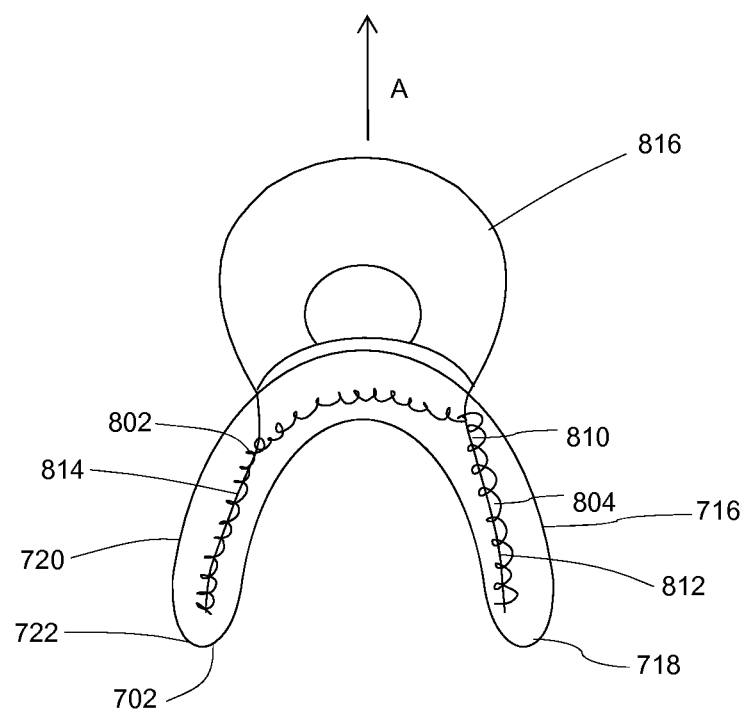
FIGS. 6A and 6B are schematic front views of the cuff electrode assembly, showing a stiffening pin that can be used in relation to embodiments of the present invention.

FIG. 6A is a schematic front view of an alternative embodiment of a cuff electrode assembly 616a in an open configuration for placement on a target nerve. In the illustrated embodiment, the cuff electrode assembly 116 includes a cuff body 702 having a first end portion 716 with a first free end 718, a second end portion 720 having a second free end 722, and a stiffening member 802. As shown, the stiffening member 802 is in the form of a helical coil extending within the cuff body 702 defining a lumen 804. As will be appreciated, the cuff electrode assembly 616a also includes at least one electrode similar or identical to the electrode 208 of the cuff electrode assemblies described herein.

Figure 6B:
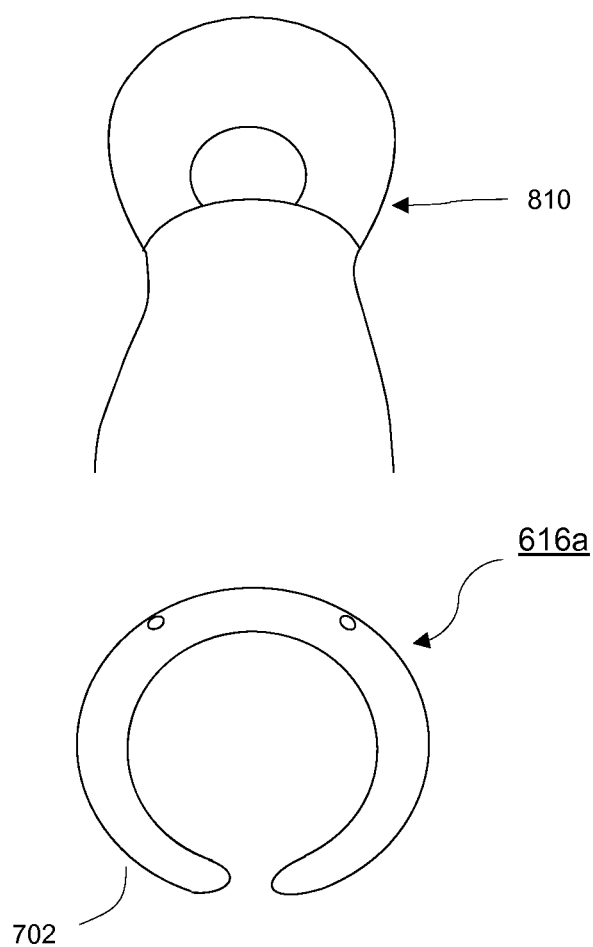

As further shown, a stiffening pin 810 is provided having a first portion 812, an opposite second portion 814, and a handle portion 816. As shown, the first and second portions 812, 814 are positioned within the lumen 804 within, respectively, the first end portion 716 and the second end portion 720 of the cuff body 702. When positioned as shown in FIG. 6A, the stiffening pin 810 operates to maintain the cuff body 702 in the open configuration for placement about the target nerve. As indicated by the arrow A in FIG. 6A, the stiffening pin 810 is removable from the cuff body 702, thus allowing the cuff body 702 to assume its closed, implanted position on the target nerve, as shown in FIG. 6B. In various embodiments, similar to the cuff electrode assemblies 116 described herein, the cuff body 702 is configured such that the first and second free ends 718, 722 can overlap one another in different planes when the cuff body 702 is in the closed configuration.

In an embodiment, the stiffening member 802 can be configured to enhance the relative stiffness of the cuff body 702, and can operate to bias the cuff body 702 toward its closed configuration. The stiffening member 802 and the stiffening pin 810 can be made of any variety of metal or polymeric materials, including those described in connection with the stiffening member 502 described previously.

Figure 7:
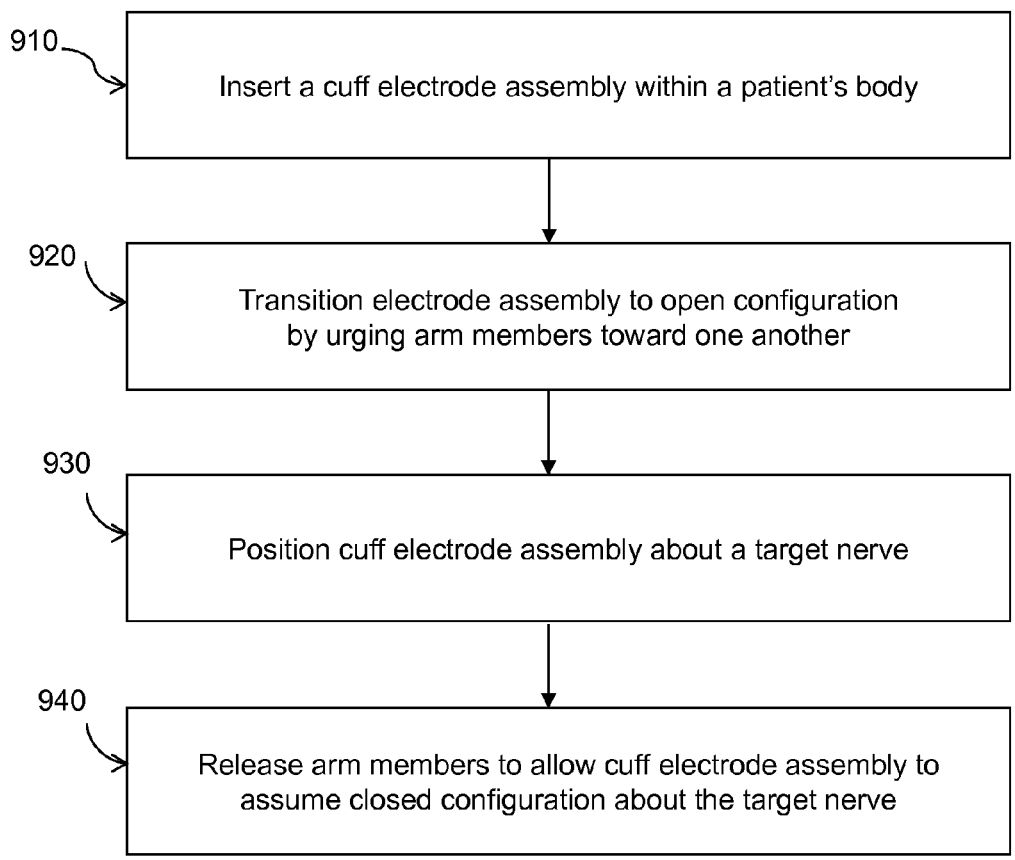
FIG. 7 is a flow chart illustrating a method for implanting a cuff electrode assembly on a target nerve.

FIG. 7 is a flow chart illustrating a method 900 for implanting a nerve cuff electrode assembly similar to the cuff electrode assembly 116a (or 116b or 16c) on a target nerve. The method 900 includes inserting the cuff electrode assembly 116a within a patient's body at step 910. In an embodiment, the cuff electrode assembly 116a is inserted to a location on or proximate the target nerve 102 (shown in FIGS. 1 and 2) such as the right vagus nerve. The method 900 further includes, at step 920, applying force to at least one of the first and second arm members 204 and 206, so as to urge the arm members 204, 206 toward one another thereby causing the first and second free ends 224 and 230 to deflect away from one another such that the cuff body 200 assumes (or transitions to) the open configuration. The method 900 further includes placing the cuff electrode assembly 116a about the target nerve 102 such that the cuff body 200 can at least partially surround the target nerve 102 at step 930. The method 900 further includes, at step 940, releasing the arm members 204, 206 to cause or allow the cuff body 200 to return to its closed configuration and thereby wrap around the target nerve 102. Upon assuming its closed configuration, the cuff electrode assembly 116a can apply a radial force on the target nerve 102 to secure the cuff electrode assembly 116a in place.

In an alternative method, the cuff electrode assembly 616a can be implanted. According to this embodiment, with the stiffening pin 810 positioned in the lumen 804 as shown in FIG. 6A, thus maintaining the cuff body 702 in the open configuration, the method includes positioning the cuff electrode assembly 616a partially about the target nerve. When positioned as desired, the clinician can then remove the stiffening pin 810 while holding the cuff body 702 in place. Upon removal of the stiffening pin 810, the cuff body 702 will tend to resume its closed configuration (as shown in FIG. 6B) and wrap at least partially around the target nerve. The foregoing steps can be repeated for each additional cuff electrode assembly 616a, if any, on the lead assembly being implanted.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

We claim:

1. A cuff electrode assembly for implantation on a target nerve, the cuff electrode assembly comprising:
   a resilient cuff body configured to be disposed about the target nerve, the cuff body having a proximal opening and a distal opening and including a first end portion having a first free end, a second end portion having a second free end, and a pinch hinge portion that extends from the proximal opening to the distal opening and connects the first end portion to the second end portion, wherein the proximal opening is defined at least in part by the pinch hinge portion and the first end portion, wherein the distal opening is defined at least in part by the pinch hinge portion and the second end portion, wherein the cuff body is pre-formed to define a closed configuration having a generally helical shape in which the cuff body is wound about a longitudinal axis, wherein the longitudinal axis extends through the distal opening and the proximal opening in a proximal-distal orientation, and wherein in the closed configuration the cuff body extends helically with the first and second end portions overlapping one another in different planes such that the first free end is proximal of the pinch hinge portion with respect to the longitudinal axis while the second free end is distal of the pinch hinge portion with respect to the longitudinal axis;

a first arm member and a second arm member each projecting radially outward from the cuff body and spaced from one another along the cuff body, wherein the cuff body is configured such that a force applied to urge the first and second arm members toward one another causes relative deflection of the second free end and the first free end so as to define an open configuration of the cuff body configured to allow the cuff body to be positioned around the target nerve; and an electrode disposed at least partially within or on the cuff body oriented to provide an electrical stimuli to the target nerve when the cuff body is disposed about the target nerve.

2. The cuff electrode assembly of claim 1, wherein the cuff body is configured to extend greater than 360 degrees about the target nerve when placed thereon in the closed configuration.

3. The cuff electrode assembly of claim 1, wherein the force applied to urge the first and second arm members toward one another is operable to reduce a degree of circumferential overlap of the first end portion and the second end portion.

4. The cuff electrode assembly of claim 1, wherein the first arm member and the second arm member form a hinge angle with the pinch hinge portion, and wherein the hinge angle is less than 180 degrees while the cuff body is in the closed configuration.

5. The cuff electrode assembly of claim 1, wherein the pinch hinge portion is located substantially equidistant from the first free end and the second free end.

6. The cuff electrode assembly of claim 1, wherein the pinch hinge portion is located closer to the first free end than to the second free end.

7. The cuff electrode assembly of claim 1, wherein the cuff body is made substantially of a flexible, electrically insulating polymer.

8. The cuff electrode assembly of claim 7, wherein the flexible insulating polymer is silicone rubber.

9. The cuff electrode assembly of claim 7, wherein the cuff body further includes a reinforcing material in the flexible, electrically insulating polymer.

10. The cuff electrode assembly of claim 7, wherein the cuff body further includes a stiffening member within the flexible, insulating polymer.

11. The cuff electrode assembly of claim 1, further comprising a stiffening member configured to urge the cuff body to return to the pre-formed closed configuration upon release of the force causing the cuff body to assume the open configuration.

12. An implantable lead assembly for stimulating a target nerve, the lead assembly comprising:

at least one cuff electrode assembly comprising:
a resilient cuff body configured to be disposed about the target nerve, the cuff body having a proximal opening and a distal opening and including a first end portion having a first free end, a second end portion having a second free end, and a pinch hinge portion that extends from the proximal opening to the distal opening and is located between the first and second end portions along a length of the cuff body, wherein the proximal opening is defined at least in part by the pinch hinge portion and the first end portion, wherein the distal opening is defined at least in part by the pinch hinge portion and the second end portion, wherein the cuff body is pre-formed to define a closed configuration having a generally helical shape in which the cuff body is wound about a longitudinal axis, wherein the longitudinal axis extends through the proximal opening and the distal opening in a proximal-distal orientation, and wherein in the closed configuration the cuff body extends helically with the first and second end portions overlapping one another in different planes such that the first free end is proximal of the pinch hinge portion with respect to the longitudinal axis while the second free end is distal of the pinch hinge portion with respect to the longitudinal axis;

a first arm member and a second arm member each projecting radially outward from the cuff body and spaced from one another along the cuff body, wherein the cuff body is configured such that a force applied to urge the first and second arm members toward one another causes relative deflection of the second free end and the first free end so as to define an open configuration of the cuff body configured to allow the cuff body to be positioned around the target nerve; and an electrode disposed at least partially within or on the cuff body oriented to provide an electrical stimuli to the target nerve when the cuff body is disposed about the target nerve; and a flexible lead body made of an insulative material, the lead body having a proximal end portion and a distal end portion, an insulated flexible conductor member at least partially disposed within the lead body, the conductor member including a distal end electrically and mechanically coupled to the electrode of the cuff electrode assembly; and a connector assembly coupled to the proximal end portion of the lead body and to the conductor member, the connector assembly configured to electrically couple the conductor member to an implantable stimulator.

13. The lead assembly of claim 12, wherein the at least one cuff assembly includes a plurality of cuff electrode assemblies, and wherein the lead further includes a plurality of insulated, flexible conductor members at least partially disposed within the lead body, and wherein an electrode of each of the plurality of cuff electrode assemblies is electrically and mechanically coupled to one of the plurality of conductor members.

14. The lead assembly of claim 13, wherein the plurality of cuff electrode assemblies are configured to be opened and implanted simultaneously.

15. The lead assembly of claim 12, wherein the cuff body is made substantially of a flexible, electrically insulating polymer.

16. The lead assembly of claim 15, wherein the cuff body further includes a stiffening member within the flexible, insulating polymer.

17. A method for implanting a cuff electrode assembly on a target nerve, the method comprising:

inserting the cuff electrode assembly within a patient's body, the cuff electrode assembly including:
a resilient cuff body configured to be disposed about the target nerve, the cuff body having a proximal opening and a distal opening and including a first end portion having a first free end, a second end portion having a second free end, and a pinch hinge portion that extends from the proximal opening to the distal opening and connects the first end portion to the second end portion, wherein the proximal opening is defined at least in part by the pinch hinge portion and the first end portion, wherein the distal opening is defined at least in part by the pinch hinge portion and the second end portion, wherein the cuff body is pre-formed to define a closed configuration having a helical shape in which the cuff body is wound about a longitudinal axis, wherein the longitudinal axis extends through the proximal opening and the distal opening in a proximal-distal orientation, and wherein in the closed configuration the cuff body extends helically with the first and second end portions overlapping one another in different planes such that the first free end is proximal of the pinch hinge portion with respect to the longitudinal axis while the second free end is distal of the pinch hinge portion with respect to the longitudinal axis;

a first arm member and a second arm member each projecting radially outward from the cuff body and spaced from one another along the cuff body, wherein the cuff body is configured such that a force applied to urge the first and second arm members toward one another causes relative deflection of the second free end and the first free end so as to define an open configuration of the cuff body configured to allow the cuff body to be positioned around the target nerve; and an electrode disposed at least partially within or on the cuff body oriented to provide an electrical stimuli to the target nerve when the cuff body is disposed about the target nerve;

applying the force to at least one of the first and second arm members to urge together the first and second arm members thereby causing the first and second free ends to deflect such that the cuff body assumes the open configuration;

with the cuff body in the open configuration, placing the cuff electrode assembly proximate the target nerve such that the cuff body at least partially surrounds the target nerve; and releasing the force to cause or allow the cuff body to close and thereby wrap substantially 360 degrees around the target nerve.

18. The method of claim 17, wherein the cuff electrode assembly further includes a stiffening member within the cuff body configured to:

stiffen the cuff body while being opened upon application of the force;

allow the cuff body to return to its closed configuration upon removal of the force; and maintain the cuff body in its closed configuration around the target nerve upon removal of the force such that the first end portion and the second end portion overlap with each other in different planes.

19. The method of claim 17, wherein the cuff electrode assembly is a first cuff electrode assembly of an implantable lead assembly including one or more additional cuff electrode assemblies, the one or more additional cuff electrode assemblies being coupled to the first cuff electrode assembly.

20. The method of claim 19, wherein the method further comprises simultaneously opening the first cuff electrode assembly and the one or more additional cuff electrode assemblies.

* * * * *